United States Patent [19]

Van Scott et al.

[11] 4,021,572

[45] May 3, 1977

[54] PROPHYLACTIC AND THERAPEUTIC TREATMENT OF ACNE VULGARIS UTILIZING LACTAMIDES AND QUATERNARY AMMONIUM LACTATES

[76] Inventors: Eugene J. Van Scott, 1138 Sewell Lane, Rydal, Pa. 19046; Ruey J. Yu, 4400 Dexter St., Philadelphia, Pa. 19128

[22] Filed: July 23, 1975

[21] Appl. No.: 598,224

[52] U.S. Cl. .............................. 424/317; 424/320; 424/329

[51] Int. Cl.² ................ A61K 31/19; A61K 31/16; A61K 31/14

[58] Field of Search .................. 424/317, 320, 329

[56] References Cited

UNITED STATES PATENTS

| | | | |
|---|---|---|---|
| 2,717,850 | 9/1955 | Schmitz | 424/319 |
| 3,068,145 | 12/1962 | Glenn | 424/320 |
| 3,096,244 | 7/1963 | Ehrhart et al. | 424/320 |
| 3,549,544 | 12/1970 | Johnson | 252/152 |
| 3,639,623 | 2/1972 | Ritschel et al. | 424/329 |
| 3,640,883 | 2/1972 | Gotte et al. | 424/320 |
| 3,666,863 | 5/1972 | Swanbeck | 424/317 |
| 3,806,593 | 4/1974 | Swanbeck et al. | 424/311 |

OTHER PUBLICATIONS

Merck Index, (1968) pp. 848-849.

*Primary Examiner*—Norman A. Drezin
*Attorney, Agent, or Firm*—LeBlanc & Shur

[57] ABSTRACT

Preventive as well as therapeutic treatment of acne vulgaris (hereafter referred to as acne) consisting of the topical application of a solution, lotion or cream containing one or more than one of the lactamides and/or quaternary ammonium lactates is disclosed. Topical application to uninvolved or involved skin has been found to achieve respectively a complete prevention or a substantial remission of acne.

28 Claims, No Drawings

PROPHYLACTIC AND THERAPEUTIC TREATMENT OF ACNE VULGARIS UTILIZING LACTAMIDES AND QUATERNARY AMMONIUM LACTATES

Acne is a skin disorder which affects most people primarily in the adolescent age range. The principal clinical manifestation of the disease is usually a variety of lesions consisting of comedones, papules, pustules, nodules, and cysts. The most frequent site of acne is the face, and to a lesser extent the back, chest and shoulders.

The basic cause of acne is still unknown. Nevertheless, considerable data on various factors involved in its pathogenesis have been accumulated in recent years. It has been known for some time that acne develops in the pilosebaceous follicle, specifically the formation of follicular plugs (comedones). The normal pilosebaceous follicle includes a fillicular canal which is open at one end to the surface of the skin through a follicular orifice and which terminates at its other end in a follicular cul de sac located in the dermal layer of the skin.

Surrounding the neck of the follicular canal are one or more multiacinar holocrine sebaceous glands which empty into the lumen of the follicular canal by means of glandular ducts. The acini of the glands have a peripheral layer of highly proliferating undifferentiated basal cells. As these basal cells are displaced from the periphery to the center of the acini by the proliferation of other basal cells, they mature and differentiate into lipid-producing cells. These cells continue to produce a variety of lipids and to store such lipids in their cytoplasm.

As lipids accumulate in the cells, the cytoplasm appears foamy, the cells enlarge, and the nuclei become distorted and disappear. The cells finally rupture, and the lipids of the cells, along with the cellular debris, form the secretory product known as sebum. In the normal state, the sebum is expelled through the glandular ducts into the follicular canal thence to the skin surface. In acne, the normal function of the pilosebaceous follicle is disrupted by an unexplained accumulation of lipids and keratinous materials in the mid-portion of the follicular canal, which accumulation ultimately becomes a comedo.

As more lipids and keratinous materials are deposited onto the comedo, the follicular canal begins to distend. If the comedo is exposed to the surface of the skin it is classified as "open"; otherwise, it is referred to as "closed". Open comendones generally are not inflammatory while closed comedones may evolve into inflamed pustules, papules, or cysts.

Therapeutic regimens for acne include local and systemic treatments, although the former is necessary in the vast majority of cases to dislodge comedones. Local treatment currently consists mainly of topical application of a variety of chemical agents which variously include sulfur, resorcinol, salicylic acid, benzoyl peroxide, Vleminckx's solution (comprising sulfur, calcium, polysulfide, and calcium thiosulfate) or retinoic acid (vitamin A acid). All the foregoing topical agents are known as "peeling" or "drying" agents which exert their therapeutic effect by causing erythema, irritation and desquamation of the skin followed by loosening and expulsion of the comedones. Oral antibiotics are often administered when microbial infections cause inflammatory papules and pustules. Two commonly used antibiotics are tetracycline and erythromycin.

Since the cause of acne is still unknown its is difficult to prevent the occurrence of acne (prophylactic treatment). Once lesions of acne are developed topical treatment with the foregoing "peeling" or "drying" agents often leads to burning or irritating of the skin. Many acne patients discontinue such treatment simply because they can no longer bear the discomfort from those agents. Although the broad spectrum antibiotics are rather effective in the management of infected acne lesions, long term use of those drugs carries a risk of systemic side effects.

It is therefore imperative to develop an efficaceous, non-toxic, non-allergenic and non-irritating substance of physiologic nature for the topical treatment of acne.

Lactic acid, $CH_3CHOHCOOH$, M.W. 90 is known to exist in D, L, and DL forms. L-Lactic acid occurs in the blood of man and animals (5–40 mg/100 ml). The skin content of L-lactic acid is reported to be approximately three times higher than that of the blood. Lactic acid concentration often increases in blood and muscle after vigorous exercise. L-lactic acid is also present in liver, kidney, thymus gland, human amniotic fluid, and other organs and body fluids. Biochemically, lactic acid is one of the key substances in carbohydrate metabolism. DL-lactic acid, also known as ordinary lactic acid, occurs in sour milk and is produced by the action of lactic acid bacteria. It is also found in molasses due to partial conversion of sugar, and is found in apples and other fruits, tomato juice, beer, wines opium, ergot, foxglove, and several higher plants.

In 1946, Stern suggested in an article appearing in *The Urologic and Cutaneous Review*, Volume 50, page 106 that certain dermatoses were related to insufficient acidity in the epidermal surface layer or coat. Accordingly, certain dermatoses including one reported case of ichthyosis were apparently successfully treated by lowering the pH of the patient's skin surface. The treatment included topical application of a 3% buffered lactic acid containing cream.

Providing an artificial acid coat has, on further investigation, been disproven as a viable treatment for dermatoses such as ichthyosis. Such wrong concept has also been corrected by our recent article: Control of keratinization with α-hydroxy acids and related compounds. I. Topical treatment of ichthyotic disorders. *Archives of Dermatology*, Volume 110, pages 586–590 (1974).

In our earlier studies of topical treatment for acne we found that lactic acid in concentrations of more than 2% in a solution could burn or irritate skin involved with acne. When lactic acid was neutralized with metal alkalis such as sodium hydroxide or potassium hydroxide, the sodium lactate or potassium lactate thus formed did not penetrate the human skin readily.

We have now discovered, however, that acne may be successfully prevented or treated with lactamides and/or quaternary ammonium lactate. Generally, the lactamide may be formed from lactic anhydride and ammonia or any primary or secondary organic amine. The quaternary ammonium lactate may be formed from lactic acid and an organic tertiary amine.

Preferred organic primary amines include any alkylamines such as methylamine and ethylamine; ethanolamines such as monoethanolamine and monoisopropanolamine; diamines such as ethylenediamine and 1,2-diamino propane.

Preferred organic secondary amines include dialkylamines such as dimethylamine and diethylamine; diethanolamine and diisopropanolamine; N-methylethanolamine and N-ethylethanolamine.

Preferred organic tertiary amines include trialkylamines such as trimethylamine and triethylamine; triethanolamine; N-methyldiethanolamine and triisopropanolamine. It has been established through extensive tests on humans having acne that topical application of a solution, lotion or cream containing from 1 to 20% of at least one of the lactamides or the quaternary ammonium lactates of this invention, and preferably from 2 to 10% thereof is therapeutically effective, when applied on a daily basis, to cause, within about 4 weeks' time, a return of the affected areas to a normal skin condition. If two or more than two mixed lactamides and/or quaternary ammonium lactates are used in a composition of this invention, the total concentration of the compounds is preferred not to exceed 10% by volume of the composition.

It has also been found in humans having extremely oily skin or having frequent occurrence of acne lesions that topical application of the aforementioned composition of the present invention is effective, when applied on a daily basis, in preventing development of acne lesions.

Accordingly, it is the object of this invention to provide a cosmetic composition containing at least one of the lactamides or the quaternary ammonium lactates, which when topically applied will reliably prevent the development of acne.

It is another object of this invention to provide a medicinal composition containing at least one of lactamide or quaternary ammonium lactate, which when topically applied will substantially alleviate the symptoms of acne.

It is still another object to provide a method for treating acne with a non-toxic solution, lotion or cream of the present invention.

It is still another object to provide a safe and efficient method for treating the symptoms of acne through regular topical application of a medicinal composition which will promote healing within about 4 weeks.

It is still another object of this invention to provide a method for formulating a cosmetic as well as medicinal composition in solution, lotion or cream which when topically applied at least daily to skin prone to lesions of acne will prevent the development of acne or result in a restoration of normal healthy skin condition.

PREPARATION OF THE THERAPEUTIC COMPOSITIONS

Commercially available lactic acid, USP grade, is a colorless, nearly odorless syrupy liquid consisting of a mixture of lactic acid ($C_3H_6O_3$) and lactic anhydride ($C_6H_{10}O_5$) equivalent to a total of not less than 85% and not more than 90% by weight of $C_3H_6O_3$. This material may be directly used for the preparation of lactamides and/or quaternary ammonium lactates in the following compositions.

To prepare the lactamides of this invention, lactic anhydride is allowed to react at room temperature with ammonia or organic amines of primary and secondary families in aqueous or alcoholic aqueous solution. The organic primary amines may include alkylamines such as methylamine, ethylamine, propylamine and butylamine; ethanolamines such as monoethanolamine and monoisopropanolamine; diamines such as ethylenediamine, 1,2-diaminopropane, 1-3-diaminopropane and N-ethanolethylenediamine. Organic secondary amines may include dialkylamines such as dimethylamine and diethylamine; diethanolamine and diisopropanolamine; N-methylethanolamine and N-ethylethanolamine.

To prepare the quaternary ammonium lactates of this invention, lactic acid is allowed to react at room temperature with organic tertiary amines in aqueous or alcoholic aqueous solution. The organic tertiary amines may include trialkylamines such as trimethylamine and triethylamine; triethanolamine; N-methyldiethanolamine; N,N-diethylethanolamine; N-ethyldiethanolamine; N,N-dimethylethanolamine; triisopropanolamine and N,N-dioctylethanolamine.

Generally, the lactamide or quaternary ammonium lactate formed in the solution needs no isolation procedure and may be directly incorporated into the therapeutic composition.

The initial concentration of lactic anhydride and/or lactic acid may range from 1 to 20% by volume of the total composition. The preferred concentration range, however, is from 2 to 10%.

Ordinarily water is used as a solvent in the preparation of the composition. To improve the suitability of the composition for topical use on human skin ethanol and propylene glycol may be added to the aqueous solution. The ratio of each vehicle may vary; however, the preferred concentration of ethanol and propylene glycol should not exceed 70% and 30% respectively.

Generally, the concentration of ammonia or organic amine used for the preparation of lactamine and/or quaternary ammonium lactate may range from 1 to 20% by volume of the total composition. The preferred composition range, however, is from 1 to 10%. The pH of the composition may vary from 3 to 8, the preferred pH, however, is from 3.5 to 7.0.

In the methods for formulating compositions of the present invention two or more than two different lactamides or quaternary ammonium lactates may also be utilized in the composition.

The therapeutic composition may also be prepared in a form of lotions or creams. In these instances, cosmetically acceptable ingredients are incorporated into the formulation and lotions or creams are readily prepared.

The following are illustrative examples of formulations of compositions according to this invention. Although the examples utilize only representative compounds in the interest of clarity, it should be understood that the following examples are illustrative and not limited. Therefore, any of the above organic amines may be substituted according to the teachings of this invention in the following formulations.

EXAMPLE 1

Lactic acid, USP grade 11 mls was dissolved in 10 mls of water and the solution admixed with 50 mls of ethanol and 10 mls of propylene glycol. Concentrated ammonium hydroxide solution ($NH_3$, 29%), 7 mls was added to the solution. Sufficient water was then added to make 100 mls of composition. This composition had a pH of 6.4.

EXAMPLE 2

Lactic acid, USP grade 5 mls was dissolved in 10 mls of water and the solution admixed with 50 mls of ethanol and 20 mls of propylene glycol. Ethanolamine 2.5 mls was added to the solution. Sufficient water was then added to make 100 mls of composition. This composition had a pH of 5.

EXAMPLE 3

Lactic acid, USP grade 5 mls was dissolved in 10 mls of water and the solution admixed with 50 mls of ethanol and 20 mls of propylene glycol. Diethanolamine 4 mls was added to the solution. Sufficient water was then added to make 100 mls of composition. This composition had a pH of 5.6.

EXAMPLE 4

Lactic acid, USP grade 5 mls was dissolved in 10 mls of water and the solution admixed with 50 mls of ethanol and 20 mls of propylene glycol. Triethanolamine, 5 mls was added to the solution. Sufficient water was then added to make 100 mls of composition. This composition had a pH of 5.2.

EXAMPLE 5

| Part A: | Polyoxyethylene sorbitan monooleate (hereinafter Tween 80)* | 50 grams |
| --- | --- | --- |
|  | Cetyl alcohol | 220 grams |
|  | Cholesterol | 4 grams |
|  | Squalene | 2 grams |
| Part B: | Water | 550 mls |
|  | Propylene glycol | 100 mls |
|  | Lactic acid | 50 mls |
|  | Ethanolamine | 20 mls |

*Tween 80 is a trademark for a particular brand of poloxy ethylene (20) sorbitan monooleate. See Merck Index (1968) pp. 848–849 for a complete description of said material.

Heat part A to 70° C and heat Part B to 75° C. Add Part B slowly to Part A with agitation. Continue agitation until the mixture is congealed. The water-washable cream thus prepared had a pH of 4.5

EXAMPLE 6

| Part A: | Tween 80 | 50 grams |
| --- | --- | --- |
|  | Cetyl alcohol | 150 grams |
|  | Stearyl alcohol | 50 grams |
|  | Squalene | 5 grams |
| Part B: | Water | 570 mls |
|  | Propylene glycol | 100 mls |
|  | Lactic acid | 30 mls |
|  | Triethanolamine | 25 mls |
|  | Mannitol | 20 mls |

Heat Part A to 75° C and heat Part B to 80° C. Add Part B slowly to Part A with agitation. Continue agitation until the mixture is congealed. The water-washable cream thus prepared has a pH of 4.

EXAMPLE 7

| Part A: | Tween 80 | 50 grams |
| --- | --- | --- |
|  | Cetyl alcohol | 150 grams |
|  | Stearyl alchol | 50 grams |
|  | Squalene | 5 grams |
|  | Cholesterol | 5 grams |
| Part B: | Water | 560 mls |
|  | Propylene glycol | 100 mls |
|  | Lactic acid | 40 mls |
|  | Ethanolamine | 20 mls |
|  | Mannitol | 20 mls |

Heat Part A to 75° C. and heat Part B to 80°. Add Part B slowly to Part A with agitation. Continue agitation until the mixture is congealed. The water-washable cream thus prepared has a pH of 4.6.

TEST RESULTS

Each of the aforementioned compositions was initially subjected to a series of screening tests on rhino mice and ICR white mice. The prepared compositions were topically applied to the backs of mice once daily for a period of 1, 2 or 3 weeks. In the case of the ICR mice, hair was removed by plucking the test site before topical applications of test composition were initiated. Each test preparation was applied to 5 rhino mice and 10 ICR mice.

At the end of 1, 2, or 3 weeks, biopsy samples of skin were taken from the test sites, fixed in 10% buffered formalin and embedded in paraffin. Histologic sections were cut at $6\mu$, stained with hematoxyline and eosin and examined for histologic features under a microscope to determine the effects of topically applied test composition on thickness and changes in the epidermis, the epidermal granular layer and the stratum corneum.

In addition, each composition was further treated for toxicity by subcutaneous injection of various concentrations into ICR mice. Ten ICR mice were employed for each test composition. The aforementioned screening tests indicated that all compositions listed in the above examples were non-toxic.

A total of 84 patients with acne were divided into 7 groups of 12 patients each. Each group of 12 patients was instructed to apply a different one of the preparations listed in the above examples topically twice daily on the skin of the face for 4 weeks. Eighty to 100 percent of the patients tested (at least 10 in each group) showed substantial reduction in the number of acne lesions after 4 weeks of topical treatment. On continued use it was also discovered that daily topical application of the above preparation could prevent the development of new acne lesions.

Each of the preparations of the present invention was observed, on continued daily topical use, to be nonirritating to the skin, non-allergenic and provocative of no signs indicative of potential toxicity.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by United States Letters Patent is:

1. A non-irritating therapeutic composition for alleviating the symptoms of acne in humans and for preventing the recurrence thereof comprising: as an active ingredient, a therapeutically effective amount of a product prepared by reacting, in aqueous or alcoholic aqueous solution at room temperature, lactic acid or lactic anhydride and a base selected from the group consisting ammonium hydroxide, an organic primary, secondary, or tertiary alkylamine, alkanol amine, diamine, dialkylamine, dialkanolamine, alkylalkanol amine, trialkylamine, trialkanol amine, dialkyl alkanol amine, and alkyl dialkanolamine wherein the alkyl or alkanol substituent has from 1 to 8 carbon atoms, in a pharmaceutically acceptable vehicle for topical application.

2. The composition of claim 1 wherein the active ingredient is present in a concentration of from 1 up to about 20 percent by volume of the total composition.

3. The composition of claim 1 wherein the active ingredient is present in a concentration of from 2 up to about 10 percent by volume of the total composition.

4. The composition of claim 1 wherein the active ingredient comprises a product prepared by reacting lactic acid or lactic anhydride and a member selected from the group consisting of ammonium hydroxide, methylamine, ethylamine, monoethanolamine, monoisopropanolamine, ethylenediamine, 1,2-diaminopropane, dimethylamine, diethanolamine, diisopropanolamine, N-methylethanolamine, N-ethylethanolamine, trimethylamine, triethylamine, triethanolamine, N-methyldiethanolamine, and triisopropylamine.

5. The composition of claim 1 wherein the active ingredient comprises a product prepared by reacting lactic acid or lactic anhydride and a member selected from the group consisting of ammonium hydroxide, methylamine, ethylamine, propylamine, butylamine, monoethanolamine, monoisopropanolamine, ethylenediamine, 1,2-diaminopropane, 1,3-diaminopropane, N-ethanolethylenediamine, dimethylamine, diethylamine, diethanolamine, diisopropanolamine, N-methylethanolamine, N-ethylethanolamine, trimethylamine, triethylamine, triethanolamine, N-methyldiethanolamine, N,N-diethanolamine, N-ethyldiethanolamine, N-N-dimethylethanolamine, triisopropanolamine, and N-N-dioctylethanolamine.

6. The composition of claim 1 wherein the vehicle is at least one member selected from the group consisting of water, ethanol, and propylene glycol present therein in a concentration of up to 99, 70, and 30 percent, respectively.

7. The composition of claim 1 wherein the pH thereof is from about 3 to about 8.

8. The composition of claim 1 wherein the pH thereof is from about 3.5 to about 7.

9. A non-irritating therapeutic composition for alleviating the symptoms of acne in humans and for preventing the recurrence thereof comprising, in approximate parts by volume: a product prepared by reacting, in aqueous or alcoholic aqueous solution at room temperature, 11 parts lactic acid, and 7 parts concentrated ammonium hydroxide solution admixed with 10 parts water, 50 parts ethanol, and 10 parts propylene glycol diluted with sufficient additional water to make 100 parts of said composition.

10. A nonirritating therapeutic composition for alleviating the symptoms of acne in humans and for preventing the recurrence thereof comprising, in approximate parts by volume: a product prepared by reacting, in aqueous or alcoholic aqueous solution at room temperature, 5 parts lactic acid, and 2.5 parts ethanolamine admixed with 10 parts water, 50 parts ethanol, and 20 parts propylene glycol, diluted with sufficient water to make 100 parts of said composition.

11. A non-irritating composition for alleviating the symptoms of acne in humans and for preventing the recurrence thereof comprising, in approximate parts by volume: a product prepared by reacting, in aqueous or alcoholic aqueous solution at room temperature, 5 parts lactic acid, and 4 parts diethanolamine admixed with 10 parts water, 50 parts ethanol, and 20 parts propylene glycol, diluted with sufficient water to make 100 parts of said composition.

12. A non-irritating therapeutic composition for alleviating the symptoms of acne in humans and for preventing the recurrence thereof comprising, in admixture: an ointment base comprising, in approximate parts by weight, 50 parts polyoxyethylene (20) sorbitan monooleate, 220 parts cetyl alcohol, 4 parts cholesterol, and 2 parts squalene; and a liquid comprising, in approximate parts by volume, 550 parts water, 100 parts propylene glycol, admixed with a product prepared, by reacting, in aqueous or alcoholic aqueous solution at room temperature, 50 parts lactic acid and 20 parts ethanolamine, said base and liquid being present in a weight-volume ratio of 276 grams of said base to 720 mls of said liquid.

13. A non-irritating therapeutic composition for alleviating the symptoms of acne in humans and for preventing the recurrence thereof comprising, in admixture: an ointment base comprising, in approximate parts by weight, 50 parts polyoxyethylene (20) sorbitan monooleate, 150 parts cetyl alcohol, 50 parts stearyl alcohol, 5 parts squalene and 5 parts cholesterol; and a liquid comprising, in approximate parts by volume, 560 parts water, 20 parts mannitol and 100 parts propylene glycol, admixed with a product prepared by reacting, in aqueous or alcoholic aqueous solution at room temperature, 40 parts lactic acid, and 20 parts ethanolamine, said base and said liquid present in a weight-volume ratio of 260 grams base to 740 mls liquid.

14. A non-irritating therapeutic composition for treatment of the symptoms of acne in humans and for preventing the recurrence thereof comprising, in admixture: an ointment base comprising, in approximate parts by weight, 50 parts Tween 80, 150 parts cetyl alcohol, 50 parts stearyl alcohol, 5 parts squalene and 5 parts cholesterol; and a liquid comprising, in approximate parts by volume, 560 parts water, 100 parts propylene glycol, 40 parts lactic acid, 20 parts ethanolamine, and 20 parts mannitol, said base and said liquid present in a weight-volume ratio of 260 grams base to 740 mls liquid.

15. A non-irritating method for alleviating the symptoms of acne in humans and for preventing the recurrence thereof comprising: topically applying to involved areas of the body and to areas thereof susceptible to acne lesions, an effective amount of a composition comprising: a therapeutically effective amount of a product prepared by reacting, in aqueous or alcoholic aqueous solution at room temperature, lactic acid or lactic anhydride and a base selected from the group consisting of ammonium hydroxide, an organic primary, secondary, or tertiary alkylamine, alkanolamine, diamine, dialkylamine, dialkanolamine, alkylalkanolamine, trialkylamine, trialkanol amine, Dialkyl alkanol amine, or alkyl dialkanolamine wherein the alkyl or alkanol substituent has from 1 to 8 carbon atoms, in a pharmaceutically acceptable vehicle.

16. The method of claim 15 wherein the reaction product is present in a concentration of from 1 up to about 20 percent by volume of the total composition.

17. The method of claim 15 wherein the reaction product is present in a concentration of from 2 up to about 10 percent by volume of the total composition.

18. The method of claim 15 wherein the product comprises a product prepared by reacting lactic acid or lactic anhydride and a member selected from the group consisting of ammonium hydroxide, methylamine, ethylamine, monoethanolamine, monoisopropanolamine, ethylenediamine, 1,2-diaminopropane, dimethylamine, diethylamine, diethanolamine, diisopropanolamine, N-methylethanolamine, N-ethylethanolamine, triethylamine, triethanolamine, N-methyldiethanolamine, and triisopropylamine.

19. The method of claim 15 wherein the product comprises a product prepared by reacting lactic acid or lactic anhydride and a member selected from the group consisting of ammonium hydroxide, methylamine, ethylamine, propylamine, butylamine, monoethanolamine, monoisopropanolamine, ethylenediamine, 1,2-diaminopropane, 1,3-diaminopropane, N-ethanolethylenediamine, dimethylamine, diethylamine, diethanolamine, diisopropanolamine, N-methylethanolamine, N-ethylethanolamine, trimethylamine, triethylamine, triethanolamine, N-methyldiethanolamine, N,N-diethanolamine, N-ethyldiethanolamine, N-N-dimethylethanolamine, triisopropanolamine, and N,N-dioctylethanolamine.

20. The method of claim 15 wherein the vehicle is at least one member selected from the group consisting of water, ethanol, and propylene glycol present therein in a concentration of up to 99, 70, and 30 percent, respectively.

21. The method of claim 15 wherein the pH thereof is from about 3 to about 8.

22. The method of claim 15 wherein the pH thereof is from about 3.5 to about 7.

23. A non-irritating method for alleviating the symptoms of acne in humans and for preventing the recurrence thereof comprising: topically applying to involved areas of the body and to areas thereof susceptible to acne lesions an effective amount of the composition comprising in approximate parts by volume: a product prepared by reacting, in aqueous or alcoholic aqueous solution at room temperature, 11 parts lactic acid, and 7 parts concentrated ammonium hydroxide admixed with 10 parts water, 50 parts ethanol, and 10 parts propylene glycol, diluted with sufficient additional water to make 100 parts of said composition.

24. A non-irritating method for alleviating the symptoms of acne in humans and for preventing the recurrence thereof comprising: topically applying to involved areas of the body and to areas thereof susceptible to acne lesions an effective amount of a composition comprising in approximate parts by volume: a product prepared by reacting, in aqueous or alcoholic aqueous solution at room temperature, 5 parts lactic acid, and 2.5 parts ethanolamine admixed with 10 parts water, 50 parts ethanol, and 20 parts propylene glycol, diluted with sufficient water to make 100 parts of said composition.

25. A non-irritating method for alleviating the symptoms of acne in humans and for preventing the recurrence thereof comprising: topically applying to involved areas of the body and to areas thereof susceptible to acne lesions an effective amount of a composition comprising, in approximate parts by volume: a product prepared by reacting, in aqueous or alcoholic aqueous solution at room temperature, 5 parts lactic acid, and 4 parts diethanolamine admixed with 10 parts water, 50 parts ethanol, and 20 parts propylene glycol, diluted with sufficient water to make 100 parts of said composition.

26. A non-irritating method for alleviating the symptoms of acne in humans and for preventing the recurrence thereof comprising: topically applying to involved areas of the body and to areas thereof susceptible to acne lesions an effective amount of a composition comprising, in admixture: an ointment base comprising in approximate parts by weight, 50 parts polyoxyethylene (20) sorbitan monooleate, 220 parts cetyl alcohol, 4 parts cholesterol, and 2 parts squalene; and a liquid comprising in approximate parts by volume, 550 parts water, and 1-0 parts propylene glycol, admixed with a product prepared by reacting, in aqueous or alcoholic aqueous solution at room temperature, 50 parts lactic acid, and 20 parts ethanolamine, said base and liquid being present in a weight-volume ratio of 276 grams of said base to 720 mls of said liquid.

27. A non-irritating method for alleviating the symptoms of acne in humans and for preventing the recurrence thereof comprising: topically applying to involved areas of the body and to areas thereof susceptible to acne lesions an effective amount of a composition comprising, in admixture: an ointment base comprising, in approximate parts by weight, 50 parts polyoxyethylene (20) sorbitan monooleate, 150 parts cetyl alcohol, 50 parts stearyl alcohol, and 5 parts squalene, and a liquid comprising, in approximate parts by volume, 570 parts water, 20 parts mannitol and 100 parts propylene glycol, admixed with a product prepared by reacting, in aqueous or alcoholic aqueous solution at room temperature, 30 parts lactic acid and 25 parts triethanolamine, said base and said liquid being present in a weight-volume ratio of 255 grams base to 745 mls liquid.

28. A non-irritating method for alleviating the symptoms of acne in humans and for preventing the recurrence thereof comprising: topically applying to involved areas of the body and to areas thereof susceptible to acne lesions an effective amount of a composition comprising, in admixture, an ointment base comprising, in approximate parts by weight, 50 parts polyoxyethylene (20) sorbitan monooleate, 150 parts cetyl alcohol, 50 parts stearyl alcohol, 5 parts squalene, and 5 parts cholesterol, and a liquid comprising, in approximate parts by volume, 560 parts water, 20 parts mannitol, and 100 parts propylene glycol, admixed with a product prepared by reacting, in aqueous or alcoholic aqueous solution at room temperature, 40 parts lactic acid, and 20 parts ethanolamine, said base and liquid present in a weight-volume ratio of 260 grams base to 740 mls liquid.

* * * * *

UNITED STATES PATENT AND TRADEMARK OFFICE
CERTIFICATE OF CORRECTION

PATENT NO. : 4,021,572
DATED : May 3, 1977
INVENTOR(S) : Eugene J. Van Scott, Ruey J. Yu It is certified that error appears in the above-identified patent and that said Letters Patent are hereby corrected as shown below:

Column 2, line 3, "its" should read --it--.

Column 2, line 31, after "wines" insert --,--.

Column 6, line 17, "treated" should read --tested--.

Signed and Sealed this nineteenth Day of July 1977

[SEAL]

Attest:

RUTH C. MASON
Attesting Officer

C. MARSHALL DANN
Commissioner of Patents and Trademarks